(12) United States Patent
Hurst et al.

(10) Patent No.: US 6,721,754 B1
(45) Date of Patent: Apr. 13, 2004

(54) SYSTEM AND METHOD FOR DATABASE SIMILARITY JOIN

(75) Inventors: John R. Hurst, San Diego, CA (US); Scott G. Hutton, Poway, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/301,811

(22) Filed: Apr. 28, 1999

(51) Int. Cl.[7] .......................... G06F 7/00; G06F 17/00; G06F 19/00; G01N 33/48; G01N 33/50
(52) U.S. Cl. .......................... 707/102; 702/19; 702/27
(58) Field of Search .............................. 702/19, 20, 22, 702/27; 707/4, 5, 102

(56) References Cited

U.S. PATENT DOCUMENTS

| | | | |
|---|---|---|---|
| 5,751,605 A | 5/1998 | Hurst et al. | 364/496 |
| 5,953,727 A | * 9/1999 | Maslyn et al. | 707/104 |
| 5,983,220 A | * 11/1999 | Schmitt | 707/5 |
| 6,240,374 B1 | * 5/2001 | Cramer et al. | 703/11 |

FOREIGN PATENT DOCUMENTS

| | | |
|---|---|---|
| WO | WO98/20437 | 5/1998 |
| WO | WO98/48998 | 10/1998 |

OTHER PUBLICATIONS

Downs et al., "Evaluation of similarity searching methods using activity and toxicity data," *Chemical Structures 2*, pp. 409–421 (1993).

Grethe et al., "Similarity searching in the development of new bioactive compounds, an application," *Chemical Structures 2*, pp. 399–407 (1993).

Matter et al., "Compound libraries for lead discovery," *Chemistry Today* pp. 9–15 (1996).

Patterson et al., "Neighborhood Behavior: A useful concept for validation of 'Molecular Diversity' descriptors," *American Chemical Society* 39:3049–3059 (1996).

Winkler et al., "Holographic QSAR of benzodiazepines," *CSIRO Division of Molecular Science, Monash University, Department of Chemistry*.

Kearsley, et al, "Chemical Similarity Using Physiochemical Property Descriptors," J Chem Ind. Computer Sci. (1996) 38:118–127.

* cited by examiner

*Primary Examiner*—Marianne P. Allen
(74) *Attorney, Agent, or Firm*—Michael P. Straher; Cozen O'Connor; Ann A. Wieczorek (57) ABSTRACT

Disclosed herein are systems and methods for information organization whereby characteristics regarding entities are inferred from the characteristics of similar entities. This is referred to herein as a "fuzzy similarity join" and is exemplified using a chemical similarity join. The disclosed systems and methods are particularly useful for chemical compound analysis in the area of pharmaceutical development.

1 Claim, 7 Drawing Sheets

| DEPT ID | DEPT. NAME | BUDGET CODE | LOCATION | MANAGER ID |
|---|---|---|---|---|
| 1001 | ACCOUNTING | 11-234 | BUILDING A | 205 |
| 1002 | RESEARCH | 11-259 | BUILDING Z | 133 |
| 1003 | G & A | 11-532 | BUILDING A | 1 |
| 1004 | DEVELOPMENT | 13-743 | BUILDING B | 152 |
| 1005 | LEGAL | 12-675 | BUILDING A | 345 |

*Fig. 4A*

| EMPLOYEE ID | NAME | SS NO. | OFFICE | DEPT ID |
|---|---|---|---|---|
| 103 | SMITH, JOE | 303-30-3030 | A123 | 1001 |
| 205 | JAMES, JIM | 404-40-4040 | A302 | 1004 |
| 152 | DOE, JANE | 505-50-5050 | C128 | 1004 |
| 666 | WILLIAMS, BILL | 606-60-6060 | H1 | 1005 |
| 133 | DAVIDSON, DAVE | 707-70-7070 | Z222 | 1004 |

*Fig. 4B*

| NAME | OFFICE | EMPLOYEE ID | DEPT. NAME |
|---|---|---|---|
| SMITH, JOE | A123 | 103 | ACCOUNTING |
| JAMES, JIM | A302 | 205 | DEVELOPMENT |
| DOE, JANE | C128 | 152 | DEVELOPMENT |
| WILLIAMS, BILL | H1 | 345 | LEGAL |
| DAVIDSON, DAVE | Z222 | 133 | DEVELOPMENT |

*Fig. 4C*

| STRUCTURE | PRICE PER GRAM | PURITY PERCENT |
|---|---|---|
| CH3CH2OCH3 | $50 | 99 |
| CH3CH2OH | $30 | 40 |
| CH3CH2CH2CH2CH2CH3 | $1.60 | 75 |

*Fig. 5A*

| STRUCTURE | Rat LD 50 |
|---|---|
| CH3CH2OH | 2 |
| CH3CH2CH2CH2CH2CH3 | 40,000 |

*Fig. 5B*

| Structure | Price per Gram | Purity percent | Rat LD 50 |
|---|---|---|---|
| CH3CH2OH | $30 | 40 | 2 |
| CH3CH2CH2CH2CH2CH3 | $1.60 | 75 | 40,000 |

SYSTEM AND METHOD FOR DATABASE SIMILARITY JOIN

BACKGROUND OF THE INVENTION

1. Field of the Invention

The present invention relates generally to information databases, specifically to database similarity joins and more specifically to a system and method for information organization whereby characteristics regarding entities are inferred from the characteristics of similar entities. This is referred to herein as a "fuzzy similarity join" and is exemplified using a chemical similarity join.

2. Background Information

A. Development of Drug Candidates

Chemists, biologists and other users regularly create and test series of chemical compounds in investigating and verifying a hypothesis. In this process, the users often seek to obtain chemical compounds exhibiting certain characteristics, or behaving according to certain metrics, and may seek to synthesize compounds having similar characteristics or behavior patterns.

The process of searching for a chemical compound of some commercial value usually starts with broad-based selection and testing. An example of this is the high-throughput screening typically used in the initial phase of pharmaceutical agent discovery. Pharmaceutical discovery is used as an example, but the same type of process is used for agricultural chemical discovery and material science research, as well as in other related fields.

In High-throughput Screening ("HTS"), the number of compounds examined and tested for a desirable biological response can often range from 50,000 to 500,000, or more. The goal is to find some smaller set of compounds within the larger set that are active in a biological screen, and to treat these compounds as "leads" that can be further developed into an eventual drug candidate. The initial library of compounds tested represents many different types of chemicals.

The chemicals in the initial library can come from several sources, including those developed in-house by conventional synthesis, commercial acquisition, combinatorial chemistry, and natural product extraction. These compounds are typically placed in micro-titer plates. Typical formats for the plates include 96 and 384 well plates, but there is a trend to higher-density plates such as 1536 and 3456 well plates. These plates are typically manipulated by robots to perform the biological screening.

The screens themselves are usually based on a biological receptor. The receptor is either isolated so that binding to the receptor can be measured somewhat directly, or a cell line is engineered to give a detectable response when the receptor is modulated by the potential drug lead.

Although most initial libraries comprise thousands of chemical compounds, even the most extensive library represents a mere sub-set of the trillions (or more) of potential chemical structures that might have "drug-like" characteristics. It is estimated that the total of all compounds available from commercial vendors is currently limited to about 1 million compounds.

The list of compounds to be screened can be selected randomly from those available, or is often chosen with some intuitive "bias" of the chemists or biologists involved in a particular project. This bias can often be advantageous to the project in that chemists often have unique insights into the types of chemicals that may lead to viable drug candidates. However, and as with any bias, an intuitive approach can at times result in potential novel chemicals being overlooked.

In the last few years, the trend in the art has been to select compounds based on the diversity of the compounds within the final selection set. This process is intended to insure that many broad classes of compounds are tested. Both the measure of diversity (diversity metric) and the diversity selection method have been much discussed, but these always are dependent on a measure of similarity between two compounds. The general tendency is to choose compounds that are as different from each other as possible, but this can often lead to selection of the most chemically "unique" compounds in the set; accordingly, this approach can lead to overlooking or missing potentially active lead compounds.

In conducting these studies, researchers rarely desire selection methods that find large clusters of structurally similar compounds within the library (e.g. 5000 benzodiazepam derivatives would not be desirable). Singletons, i.e., compounds that have no similar structure in the dataset, are also generally considered undesirable because these do not allow for the opportunity to develop any structure-activity correlation information. Rather, selection methods that lead to sets of 10–15 similar structures are considered preferable. Such small sets of similar compounds allow for some analysis of the effect of small structure variations on the activity of the compounds (referred to as Structure-Activity Relationships, or, SAR studies). In addition, the small clusters help validate the screening—if 5 of 10 compounds in a small cluster evidence biological activity, because the cluster is comprised of chemically related structures, the activity is more likely to be reproducible and "optimizable."

The initial biological screening produces compounds that are generally referred to as "chemical hits" or simply "hits"—hits are compounds that have been screened in an assay and evidence biological activity above a desired threshold. These hits rarely include the final drug candidate that will be further analyzed in animal toxicology studies and, ultimately, in human clinical trials. Indeed, these hits generally represent leads that are optimized by producing small changes in their chemical structures; these changes are generally intended to improve or enhance the biological activity of the leads until a commercial candidate is identified via additional screening. These follow-on compounds can be referred to as analogues of the initial hits. This process of optimization of the hits is generally referred to as "lead follow-up."

Lead follow-up has generally been accomplished by medicinal chemists, who make small sets of analogues of some of the lead compounds. As with the initial screen that led to the initial hits, the analogues are then also tested for biological efficacy. The structure modifications that resulted in reduced activity are usually discarded in favor of those that increased the activity, and new modifications to the analogue compounds are often also made and tested. The medicinal chemist follows the leads until a compound (or a small set of compounds) is identified that has appropriate efficacy for a drug candidate.

In the last several years, the medicinal chemist has often been aided by computer-based design technologies such as Quantitative Structure Activity Relationships (QSAR). These programs use efficacy data for previously tested compounds to predict the efficacy of compounds yet to be tested. The goal of QSAR program is to give accurate predictions of the activities prior to testing the compounds.

QSAR programs have generally been successful, not in predicting the activity of the eventual drug candidate, but in allowing more efficient selection of each round of analogue synthesis. While the compounds predicted to be active by QSAR methods do not always have the activity predicted, generally these compounds have an increased chance of being active compared to the general population.

Pharmaceutical development is generally very competitive. Therefore, and almost without deviation, once a drug candidate is selected, extensive patent searches are conducted in order to insure that the candidate if or the use of the candidate is not restricted by another's patent position. Animal toxicology studies generally follow the patent search. If the animal toxicology results are acceptable, human clinical trials of the drug candidate are pursued.

The process of screening, analoging and identification of potential drug candidates can be very time consuming and expensive. Patent searching, particularly in the area of chemical compounds, can also be very time consuming and expensive. Animal toxicology studies involving the potential drug candidate can easily cost hundreds of thousands of dollars. Human clinical studies designed to establish the safety and efficacy of the potential drug candidate in humans exceed tens of millions of dollars. It is, therefore, a imperative that as much information relating to the potential drug candidate be understood as early in the process as possible such that substantial investments in time, effort and financial resources are not directed to, e.g., a potential drug candidate that is covered by the claims of a third party patent, or, e.g., a potential drug candidate that is chemically related to another compound that evidenced safety issues in human clinical studies.

B. Relational Database Systems

Relational Databases Systems ("RDS") are used prevalently throughout industry and academia to store and search information on a plethora of subjects. RDS employ a table structure to store information about the various instances of each entity. These tables have defined columns that are the attributes of each data item (rows). The data in each column can be of several types, including text, numeric, date/time, binary, etc. Data in certain columns can be indexed for faster retrieval.

In the relational model for database design, data that is repeated for several rows is usually split out into a new table/entity definition. This process is referred to as "normalization" and is generally accomplished to protect the data integrity and to save disk space. The relationship between the data in the tables is, however, maintained.

The data in RDS is generally queried by the user or application program by generating a specific query in a query-directed language. The Oracle™ system is a preferred example of a RDS. In Oracle, as in many other RDS, queries are posed using the Structured Query Language (SQL). This language allows easy retrieval of the information stored in the various tables, and allows related data in a different table to be combined. The construct of an SQL query that performs this combination of data is called a "join." The word join, in this context, is a term of art; it is noun, and not a verb. A join links rows of one table with rows of another based on some common or related columns (attributes). The join can be performed "on the fly" (i.e., the join itself is added to each query as it is created), or can be predefined to give a pseudo table, generally referred to as a "view." The view has the appearance of a new table, but generally, the view is not stored as such.

C. The Internet

The Internet provides a useful technique for making information available to a variety of individuals each of whom may be located at a variety of different locations. Indeed, within the vast Internet environment, individuals can access information tools from remote locations. Beneficially, the Internet is a preferred way for accessing information stored in relational databases, such as those described above.

The Internet, which originally came about in the late 1960's, is a computer network made up of many smaller networks spanning the entire globe. The host computers or networks of computers on the Internet allow public access to databases containing information in numerous areas of expertise. Hosts can be sponsored by a wide range of entities including, for example, universities, government organizations, commercial enterprises and individuals.

Internet information is made available to the public through servers running on an Internet host. The servers make documents or other files available to those accessing the host site. Such files can be stored in databases and on storage media such as, for example, optical or magnetic storage devices, preferably local to the host.

Networking protocols can be used to facilitate communications between the host and a requesting client. TCP/IP (Transmission Control Protocol/Internet Protocol) is one such networking protocol. Computers on a TCP/IP network utilize unique identification ("ID") codes, allowing each computer or host on the Internet to be uniquely identified. Such codes can include an IP (Internet Protocol) number or address, and corresponding network and computer names.

Created in 1991, the World-Wide Web (Web, or www) provides access to information on the Internet, allowing a user to navigate Internet resources intuitively, without IP addresses or other specialized knowledge. The Web comprises hundreds of thousands of interconnected "pages", or documents, which can be displayed on a user's computer monitor. The Web pages are provided by hosts running special servers. Software that runs these Web servers is relatively simple and is available on a wide range of computer platforms including PC's. Equally available is Web browser software, used to display Web pages as well as traditional non-Web files on the user's system.

The Web is based on the concept of hypertext and a transfer method known as "HTTP" (Hypertext Transfer Protocol). HTTP is designed to run primarily over TCP/IP and uses the standard Internet setup, where a server issues the data and a client displays or processes it. One format for information transfer is to create documents using Hypertext Markup Language (HTML). HTML pages are made up of standard text as well as formatting codes indicating how to display the page. The browser reads these codes to display the page.

Each Web page may contain pictures and sounds in addition to text. Associated with certain text, pictures or sounds are connections, known as hypertext links, to other pages within the same server or even on other computers within the Internet. For example, links may appear as underlined or highlighted words or phrases. Each link is directed to a web page by using a special name called a URL (Uniform Resource Locator). URLs enable the browser to go directly to the associated file, even if it is on another Web server.

In addition to the Internet, which allows for general, public retrieval of information, other means of accessing such information exist and are commonly utilized. For example, direct modem connections between two computers, proprietary internal networks within large institutions and organizations, etc. are equally available and useful means for accessing catalogued information stored in databases.

SUMMARY OF THE INVENTION

The present invention is directed toward a system and method for information organization whereby characteristics regarding entities can be inferred from the characteristics of similar entities. According to one aspect of the invention, database similarity joins can be used to allow characteristics or parameters regarding information contained in a first database to be inferred from characteristics or parameters regarding information contained in a second database. According to this aspect of the invention, the invention can provide for the retrieval of information that is not organized in a manner that a specific user may require or desire. This allows retrieval based upon common characteristics or a similarity between entities organized in unrelated databases. The information can be retrieved and organized in a manner that makes the information more useful to the user.

One approach that allows for such retrieval and organization is referred to as a fuzzy similarity join. According to this approach, it is not necessary that the relationship between the retrieved information be intuitively or organizationally related in the manner in which it is retrieved. Instead, the retrieval of desired information can be based upon a similarity among entities in one or more databases.

These and other aspects of the invention, which can be implemented individually or collectively, are perhaps best described in terms of an example application. For example, consider the application of chemical searching, where a scientist may wish to obtain certain information about one or more compounds of interest. According to conventional chemical database strategy, information of interest to a scientist about a compound of interest may not be readily available in a database, or may not be available at all. According to one aspect of the invention, the scientist can perform a database join to obtain information about the compound of interest from another database.

According to another aspect of the invention in this application, the scientist can perform a chemical similarity join (or fuzzy similarity join) to infer information about the compound of interest, based upon the characteristics of other parameters of "similar" compounds. According to this aspect of the invention, the chemical similarity join allows the scientist to search one or more databases to obtain information about the "similar" compounds. The scientist can use this information to infer behavior or other characteristics or parameters about the compound of interest.

In one implementation, for example, the chemical space can be defined such that a neighborhood effect exists for the property in question (for example, toxicology), then the property for the compound(s) of interest in one database can be inferred from the property data of similar compounds in another database. Thus, this aspect of the invention in this application allows two tables to be joined by a similarity comparison of the two structures. An exact match of the two structures is not required to perform the join operation.

According to another aspect of the invention, a searching tool can be used that combines actual compound data with a virtual data set to facilitate neighborhood searching around a preferred set of property metrics. The neighborhood relationship can be the basis for the similarity join.

According to another aspect of the invention, the data set can be screened to eliminate records having particular or identified properties or characteristics. Additionally, the data set can be combined with other data to allow further filtering to exclude unwanted classes of records.

According to yet another aspect of the invention, the searching tool can be linked to an ordering system, allowing the users to purchase identified items.

These and other features, advantages and aspects of the invention are discussed in more detail below.

DETAILED DESCRIPTION OF THE PREFERRED EMBODIMENTS

1. Introduction and Overview

The present invention relates generally to information databases, specifically to database similarity joins, and more specifically to a system and method for information organization whereby characteristics regarding entities are inferred from the characteristics of similar entities. The invention disclosed in this patent document is applicable and useful in the retrieval of information that is not ordinarily organized in a manner that a specific user may require or desire but, based upon common characteristics by and between entities that are organized in unrelated databases, can be retrieved and organized in a manner that makes the information far more useful than the data otherwise would be.

We refer to the approach that allows for such retrieval and organization as a "fuzzy similarity join" in that the relationship between the retrieved information is not intuitively or organizationally related in the manner in which it is retrieved; rather, this relationship is based upon the needs of a user who would otherwise be required (if possible) to laboriously search for the required data from unrelated or dispersed data sources. Indeed, unlike a more "fixed" catalogue (whether paper or electronic based), which rigidly forces a user to obtain information in a manner specifically limited in accordance with the objective of the creator of the catalogue, the present invention allows for a "fluid" retrieval of information based upon the needs and objectives of the user. In the area of chemical searching, this approach offers a substantial advance to the art.

A fuzzy similarity join would not include, for example, a traditional join which generally requires the organization and retrieval of information from datasets based upon (1) identicallity of at least one attribute that is common to the datasets that are being compared, or (2) meeting criteria set by standard elational database operators (e.g., "equals", "greater than", "less than", "contained in", "excluded from", etc.). For example, the join of FIGS. 4A, 4B, and 4C would constitute a traditional join and not a fuzzy similarity join. A fuzzy similarity join is based upon a non-traditional database operator, a non-traditional operator, in this context, evaluates the similarity of two members where "similarity" is a composite index of some or all of the attributes of the members being compared; the composite index can arbitrarily be assigned a value between zero (completely dissimilar) and less than one (not identical). For the traditional join, the composite index for two members must be exactly one (or would completely satisfy the conditions set by the standard relational operators). For the fuzzy similarity join, the composite index must have a value greater than some value predefined by the user. For example, in the preferred embodiment of a fuzzy similarity join disclosed herein (chemical similarity join), the Tanimoto coefficient functions as the composite index for a chemical similarity join, and in order to establish the chemical similarity join, a user would predefine the minimum value for the Tanimoto coefficient based upon the particular needs of the user.

Therefore, and although our disclosure focuses on a specific embodiment directed to a specific type of information, i.e., chemical compounds, our disclosure, when reviewed by those of ordinary skill in the art, will provide the opportunity to apply the invention to other areas, such as, by way of example and not limitation, biological compounds, metallurgic compounds, genetic information, health trends, population studies, political and polling trends, etc. However, for purposes of presentational efficiency, and not limitation, the focus of our disclosure is directed to a specific fuzzy similarity join, the chemical similarity join.

According to one aspect of the invention, a searching tool combines actual compound data with a virtual data set to facilitate neighborhood searching around a preferred set of property metrics.

According to another aspect of the invention, the data set can be screened to eliminate compounds having particular or identified properties. Additionally, the data set can be combined with other data to allow further filtering to exclude unwanted classes of compounds. For example, the data set can be combined with information pertaining to patent coverage, toxicology information, binding data and so on. According to another aspect of the invention, the searching tool can be linked to an ordering system, allowing the users to purchase identified compounds.

The invention and its various aspects, which can be implemented individually or collectively, is disclosed herein in terms of the Internet as a preferred interface tool. The invention as disclosed in these terms is provided for ease of discussion only. After reading the disclosure herein, it will become apparent to one of ordinary skill in the art that the present invention can be implemented in any of a number of different searching environments.

2. Library Information Integration

A most preferred embodiment of library information integration, i.e., information regarding chemical library integration, is disclosed, which, as noted above, is made in terms of the Internet environment.

Figure 1:
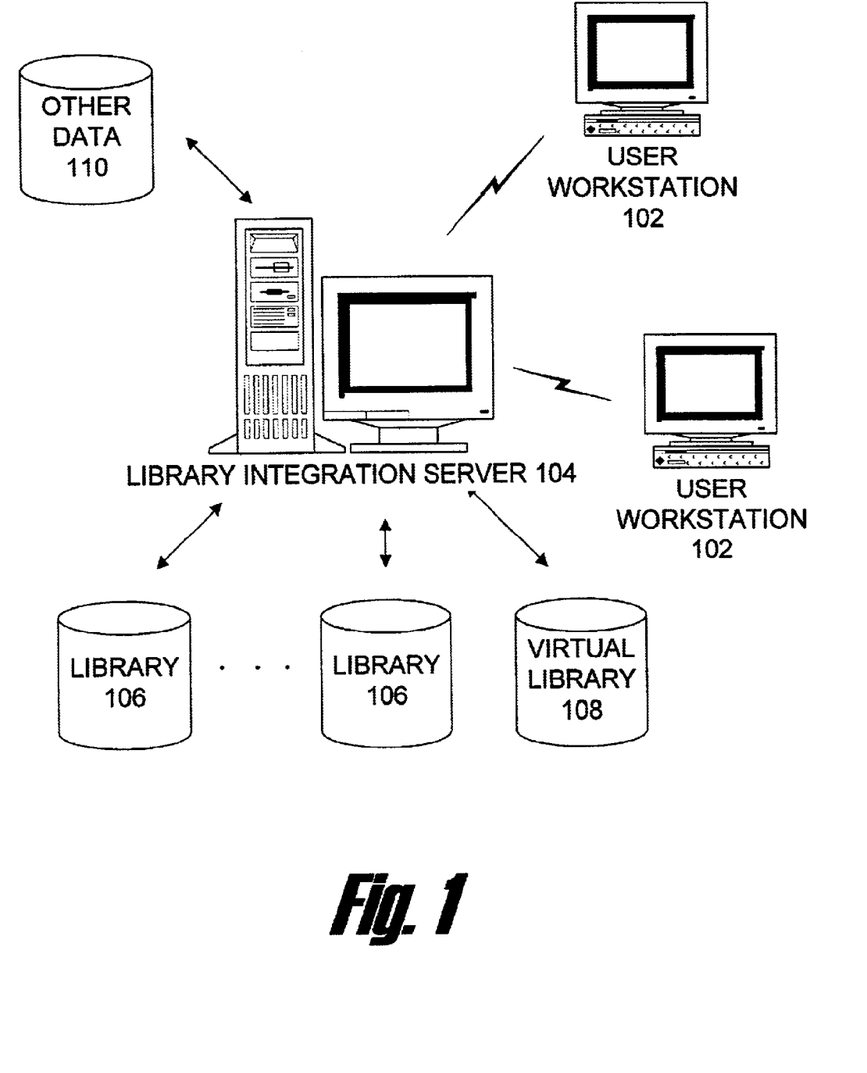
FIG. 1 is a block diagram generally illustrating one application of a library information system according to one embodiment of the invention.

FIG. 1 is a block diagram generally illustrating one application of a library integration information system according to one embodiment of the invention. The application illustrated in FIG. 1 includes a library integration server 104 having access to libraries 106, 108 as well as other data sources 110. In a preferred embodiment and in the context of chemical similarity joins, libraries 106 can include one or more chemical compound libraries that can be accessed by and searched by library integration server 104. Libraries 106 can include information about known or existing chemical compounds and can include information such as, for example, property metrics for the compounds and other information. In one embodiment where the library integration information system can also be used to purchase compounds, libraries 106 can include price, availability, and delivery information for the purchase of available compounds.

Depending on the application of the chemical library information system and the libraries 108 used in conjunction with the chemical library information system, libraries 106 can either be local to server 104 or remote therefrom. Local libraries 106 can be used to provide direct access to chemical data contained therein and can be maintained in conjunction with chemical navigation server 104. However, compound libraries 106 can exist and be maintained by third parties and be accessible to server 104 via a remote communication link, such as a dial-up link, a network, the Internet, or other communication medium. Under this scenario, the ability of the server 104 to utilize additional data sets in operation, can be expanded to external data sets.

One or more virtual compound libraries (only one illustrated) 108 are preferably included to identify a data set of virtual compounds that can be mapped with a data set of known or available compounds. "Virtual" is a term of art that generally refers to a chemical compound that may not physically exist. A virtual compound can be defined by a known synthesis pathway, such that the virtual compound can be synthesized. Preferably, a virtual compound library includes a plurality of virtual or hypothetical chemical compounds, having a set of specific properties defined by one or more property metrics. Mapping or combining a virtual data set with the known data set can be utilized to allow enhanced compound searching techniques as described in detail below. As with compound libraries 106, virtual compound library 108 can be maintained locally or at a remote location, and can be accessed by server 104 through a variety of different connection techniques.

Users wishing to access the chemical library information system can connect to server 104 via their computer or workstation 102. User workstations 102 can connect to server 104 utilizing a variety of connectivity techniques, including, for example, direct connection, network connection, or otherwise. In terms of a preferred approach, users can access server 104 from a variety of remote locations via the Internet.

A third category of library illustrated in FIG. 1 is a library containing other data 110. Other data can include data of interest relating to a chemical compound such as, for example, patent data, toxicity data, chemical compound-biological target binding data, or other data that may be of interest to a user in evaluating a chemical compound via server 104. As with libraries 106, 108, the data contained in a library 110 can be found in a common database with the other data, or can be in a separate database accessible locally or remotely by server 104.

Although libraries 106, virtual compound library 108, other data sources 110 are illustrated as a separate databases in FIG. 1, it will be apparent to one of ordinary skill in the art that the data contained in these databases can be provided in one or more physical or logical databases. Additionally, although a single server 104 is illustrated in FIG. 1, the system can be implemented utilizing one or more servers 104.

The example applications illustrated in FIG. 1 comprise at least two classes of library; compound libraries 106 and virtual compound libraries 108. As stated above, libraries 106 include information about known or existing chemicals or compounds cataloged in a library. The known compounds can be categorized according to the values of a plurality of property metrics pertaining to each compound. According to one aspect of the invention, this categorization can be accomplished by mapping the compounds into a chemistry space, and combining known compounds with virtual compounds in a chemistry space.

3. Metrics and Chemistry Spaces

Before describing the mapping of compounds in chemistry space, a mathematical introduction of "spaces" is provided. As used herein, a "space" is defined by a set of parameters and a distance function. The domain of the parameters can be the set of real or complex numbers or any subset thereof (e.g. integers, positive integers, etc.). A parameter based on a non-continuous set of numbers is called a "discrete parameter." A point in any space is defined by a specific value for each of the parameters in the space. The distance function produces a real, non-negative value for any two points in the space.

Most individuals are familiar with spaces that relate to our physically "available" living experiences—2 dimensional ("2D") and 3 dimensional ("3D") Euclidean space. Euclidean spaces have characteristics that do not apply to all spaces, and in particular, Euclidean space characteristics do not apply to spaces that include all chemical compounds ("chemistry spaces").

Chemistry spaces, unlike Euclidean spaces, are instead understood based upon space into which some or all of the possible chemicals can be mapped. The space comprises an exceedingly large number of compounds; it has been estimated that the number of organic chemical compounds with molecular weight less than 800 is about $10^{204}$.

Chemistry spaces can generally be defined by parameters that can be calculated from the chemical structure of the compound and a dissimilarity distance function based on those parameters. Parameters that can be used to define chemistry spaces can include, for example, and not limitation:

- cLogP the calculated (estimated) partition coefficient for the compound between octanol and water;
- Molecular weight (MW);
- Sterimol parameters related to size;
- Kier and Hall parameters related to the electronic nature of the structures;
- B-cut metrics such as those employed in the DiverseSolutions™ software package (U. Texas);
- Various fingerprint metrics used in commercially-available software packages from MDL, Tripos Inc., and Daylight Chemical Information Systems;
- Molecular Hologram metrics defined in the commercially-available HQSAR™ software from Tripos;

The foregoing are exemplary and by no means exhaustive.

The Unity Fingerprint space and the HQSAR Hologram space (both from Tripos, Inc. St. Louis, Mo.) exemplify the chemistry space concepts set forth above, e.g., the Unity Fingerprint is an example of a composite chemistry space metric. However, our invention does not depend on these spaces and is not limited to these spaces or metrics.

In the Unity Fingerprint space, the parameters are the various bits in the Unity fingerprint bitmap. This bitmap is generated for each chemical structure by decomposing the structure into all of its substructural fragments. A unique representation of each fragment is then hashed onto a position in the bitmap. The fingerprint bitmaps are typically 200 to 1000 bits long. When a fragment is found in a structure, the bit onto which it maps is set to 1. The fingerprint is therefore a series of bits indicating the presence of all of the fragments in the structure.

The same fragment, regardless of how encountered, should always set the same bit in the fingerprint. Thus, two structures that have many of the same fragments also have many of the same bits set in their corresponding fingerprints.

If, for example, 1000 bit fingerprints were used, the chemistry space so defined is a 1000 dimensional discrete space in which each parameter can be either 0 or 1. This space represents a 1000 dimensional "hypercube", and every possible chemical maps onto one of the vertices of this hypercube.

The distance function for this space is based on one of the similarity indices ranging from 0 to 100%. The distance is 1 minus the similarity index value (d=1−sim). The common similarity indices include the Tanimoto index, the cosine index, and several others.

The Tanimoto index is defined by: sim=C/(A+B−C), where:

C is the number of bits set (=1) in both fingerprints,

A is the number of bits set in the first fingerprint

B is the number of bits set in the second fingerprint

The Tanimoto coeffident is almost universally used, and upon application, the coefficient generally correlates with chemists' intuition about the similarity of compounds.

For ease of discussion, this document represents chemistry space as a 2D Euclidean space. This is done for convenience only. The chemistry space defined by the Unity fingerprints and the Tanimoto coefficient is not a Euclidean space, does not obey the triangle inequality, and is discrete.

In chemistry space, all of the compounds that are within a certain distance (i.e. have a similarity index of at least a certain number) define the "neighborhood" of that compound. Those compounds are said to lie within a similarity radius of the central compound, or to be within the neighborhood sphere of the compound. In non-Euclidean spaces, spheres are defined as all of the points within a certain distance of another point. Non-Euclidean spheres do not necessarily have the properties of spheres in 3D Euclidean space—they need not have a defined surface or surface area, nor volume as such. The neighborhood spheres in the figures will be represented herein as the 2D projection of a sphere (a circle) for convenience of representation only.

4. Two Dimensional Representation of a Multi-Dimensional Chemistry Space

Having introduced the concept of chemistry space, an example mapping of compounds into a multi-dimensional chemistry space is now presented.

Figure 2:
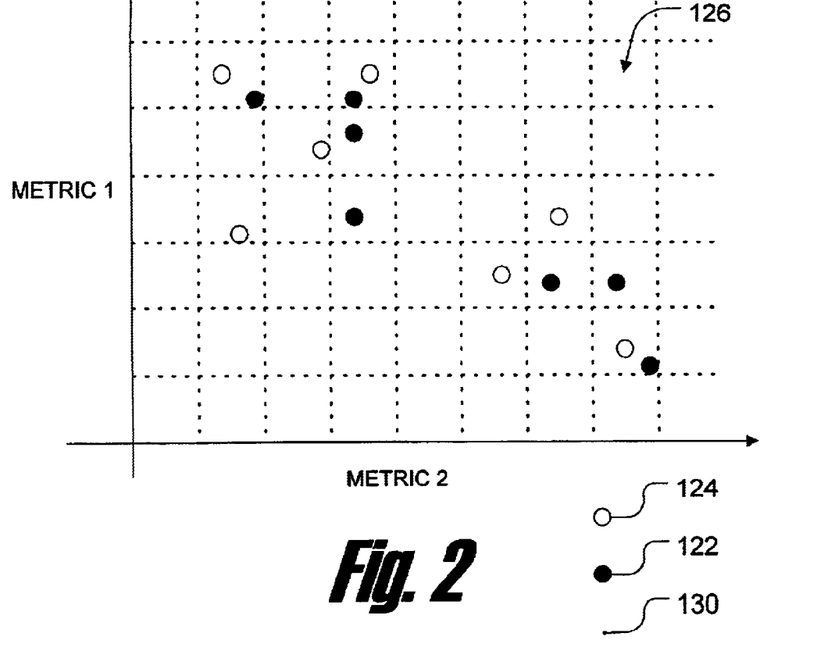
FIG. 2 is a diagram illustrating a "cell-based" neighborhood mapping of an example subset of known chemical compounds in a two-dimensional representation of multidimensional chemistry space.

FIG. 2 is a diagram illustrating a mapping of an example subset of known chemical compounds in a hypothetical, 2D chemistry space. Actual chemistry spaces are multi-dimensional and involve a multitude of metrics, rather than the two metrics (Metric 1 and Metric 2). In FIG. 2, the compounds are mapped into this space based on their specific values for two property metrics.

There are chemical database systems in existence that map compounds into chemistry space according to property metrics and that define neighborhoods for compounds according to property metric values. Examples of such databases include Tripos's Unity database systems MDL's Isis™ database system, and others. It would become apparent to one of ordinary skill in the art after reading this patent disclosure that these commercial-available databases can be used to serve as one or more libraries 106, or custom libraries can be created for a given application.

Additionally, although FIG. 2 illustrates a combination of two libraries, one or any number of libraries can be combined in a given chemistry space for navigation. Of course, given the fact that the universe of known compounds is dynamic and ever-changing, it is envisioned that libraries 106 can be updated and can change to reflect the dynamics of the chemical world. Furthermore, as this example illustrates, many different chemistry spaces can be defined and all possible chemicals can be mapped onto each of those spaces.

The compounds in FIG. 2 are represented by dots 122 and circles 124. The use of dots 122 and circles 124 illustrates that the known compounds mapped into the chemistry space can be obtained from two different databases, one for the compounds represented by dots 122 and one for the compounds represented by circles 124. As will become apparent to one of ordinary skill in the art after reading this patent document, compounds from additional databases can also be mapped into this chemistry space. As would also be apparent to one of ordinary skill in the art after reading this disclosure, compounds from one or more databases can be mapped into a multi-dimensional data space, representing up to N property metrics for the compounds.

Also illustrated in FIG. 2 are various chemical neighborhoods 126 that make up the 2D chemistry space. "Cell-based" neighborhoods 126 are illustrated in FIG. 2 as being bordered by the dashed lines. Cell-based neighborhoods are defined by partitioning the metrics into several "bins." This approach can lead to cell-based neighborhoods that include bins that do not include any compounds. Compounds 122, 124 that fall within a given cell-based neighborhood can be considered, to a certain extent, to be similar compounds.

An alternative and preferred neighborhood is based upon the points within an area or a certain distance of a given compound or virtual compound, as will be discussed with reference to FIG. 3 and larger circle 132. Compounds within circle 132 are said to be in the neighborhood of virtual compound 130A, including actual compounds 122A and 124A. It should be noted that this "distance based" neighborhood can be defined by actual or virtual compound—every compound defines its own neighborhood.

Figure 3:
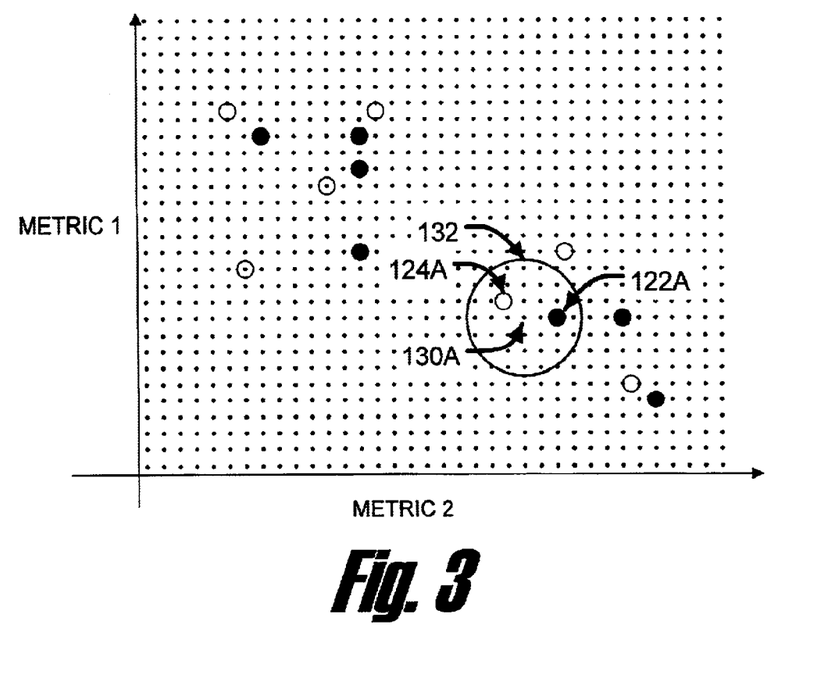
FIG. 3 is a diagram illustrating a "distance-based neighborhood" mapping of the example subset of known chemical compounds into an example dataset of virtual compounds according to one embodiment of the invention.

FIG. 3 is also a diagram illustrating an example of a virtual compound library in chemistry space, combined with the library of known chemicals as illustrated in FIG. 2. Preferably, in one embodiment of the invention, the virtual library 108 includes a large number of virtual compounds relative to the number of compounds in libraries 106, and the virtual compounds are distributed relatively uniformly across the chemistry space. As a result of this implementation, a virtual compound closely matching a given set of property metric values can be found, regardless of whether a previously synthesized compound exists with those property metric values.

As illustrated in FIG. 3, there are a relatively large number of virtual compounds 130 as compared to known compounds 122, 124. Because of this large number of virtual compounds, the virtual compounds can occupy a large number of locations within the defined chemistry space. As such, from a probabilistic perspective, it is more likely that a user will find a virtual compound corresponding to or closely matching a given set of values for desired property metrics assigned by the user. The combination of the virtual data set with the known data set allows the virtual compounds to be grouped into neighborhoods with known compounds.

5. Neighborhood Effects

Chemistry spaces can be considered useful if they exhibit "neighborhood effects" for certain relevant properties. A neighborhood effect occurs when compounds similar to a particular compound having a desired property value are more likely to have a similar property value to that of the particular compound than the general population of all compounds. As an example of a neighborhood effect, and using the UNITY fingerprints and the Tanimoto similarity index, it has been found that compounds that are 85% similar to an active compound can be 30 times more likely to be biologically active than compounds chosen randomly.

Chemistry spaces that have been found to produce neighborhood effects for biological activity and toxicology include the b-cut spaces of DiverseSolutions (U. Texas), the Fingerprint spaces (Tripos, MDL, Daylight), and the SAR spaces in Cerius2 (MSI). However, it should be noted that certain properties and metrics do not produce neighborhood effects. For example, for a chemistry space based on molecular weight and cLogP, one would not be expected find that the neighbors of an active compound have an enhanced likelihood of being biologically active as well. Thus, the space defined by molecular weight and cLogP does not produce a neighborhood effect for biological activity. Those of ordinary skill in the art are credited with the ability to establish neighborhood effect criteria suitable for the particular needs of the artisan.

6. Fuzzy Similarity Join; Chemical Similarity Join

A chemical similarity join can be used to help identify compounds that may be of interest to a user. Prior to disclosing chemical similarity join, however, it is useful to first describe the concept of join operations in relational database systems.

Figure 4A:
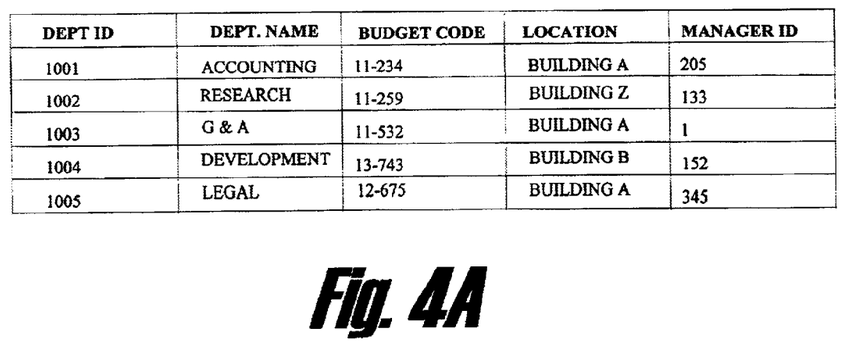
FIG. 4A is a diagram illustrating an example table that may be used to store information about various departments in a company.

In relational database systems, tables are used to store records of related information. Each table represents occurrences of an entity-type, such that the attributes of the table also define the entity. For example, a table may be used to store information about the various departments in a company. The attributes of the table might include items such as a department ID number, the department name, the budget code, manager name, building location, etc. One such example table is illustrated in FIG. 4A.

Figure 4B:
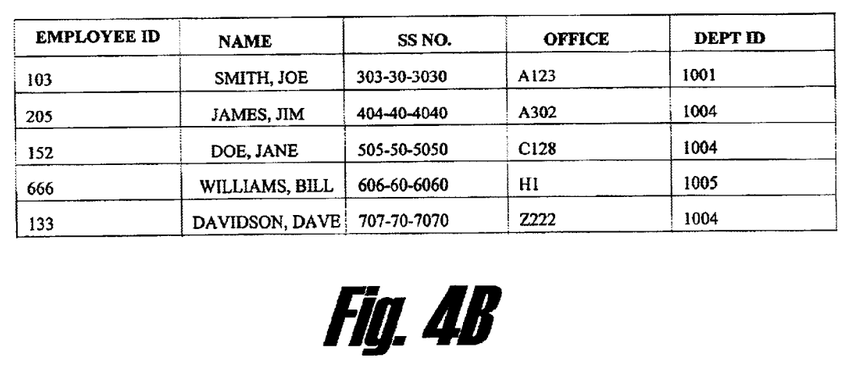
FIG. 4B is a diagram illustrating an example table that may include information about the employees of a company, including the employee ID number, social security number, name, department ID number, office location, title, etc.

Another table might contain information about the employees of a company, including the employee ID number, social security number, name, department ID number, office location, title, etc. One such example table is illustrated in FIG. 4B.

The information in these tables can be combined to produce information of interest using a database "join". A join associates rows in one table to those in another based on relationships between values of certain columns for the records. For example, the Employee table can be joined to the department table to give a new pseudo table (called a View) that gives the Department name for each employee. An example of a Structured Query Language query that would accomplish the creation of the join could be:

Select name, office, employee ID, department name from department table, employee table where department table. dept. ID=employee table.dept. ID.

Figure 4C:
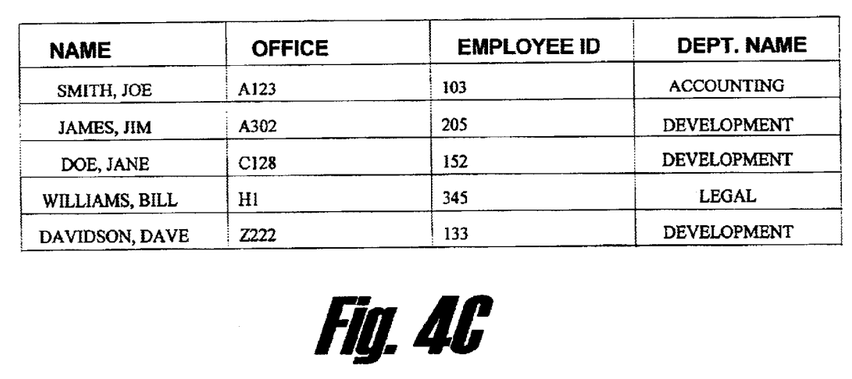
FIG. 4C is a diagram illustrating an example table that may result from an example SQL query calling for a database join.

The resulting view table that would be created using such a SQL query may look like that illustrated in FIG. 4C.

Relational databases can be used to store information about various compound libraries in a similar manner. In the context of chemical compounds and information related thereto, different libraries might have different attributes, including chemical structure, vendor, price, location, toxicology data, bio-screening data, etc. The information in various libraries can be joined to increase the value of the information. For example, one table might contain data on compounds available from Vendor A, and a second table might have Rat $LD_{50}$ data of a set of compounds. The tables can be joined to provide information about compounds that are available and have good toxicology results. In one embodiment, this join can be accomplished using the chemical structure.

Figure 5A:
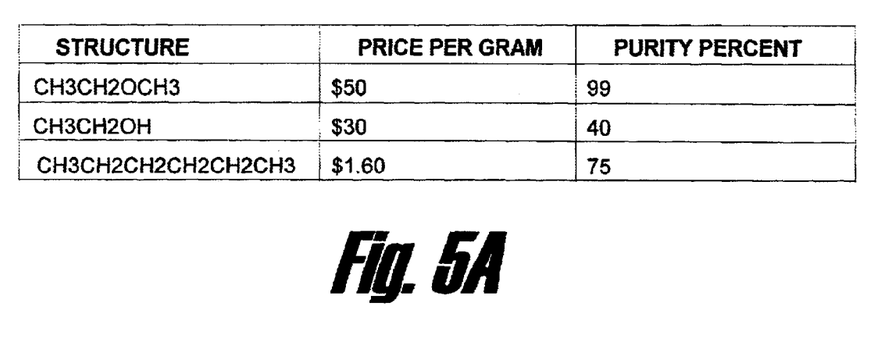
FIG. 5A is a diagram illustrating an example Vendor table for chemical compounds.
Figure 5B:
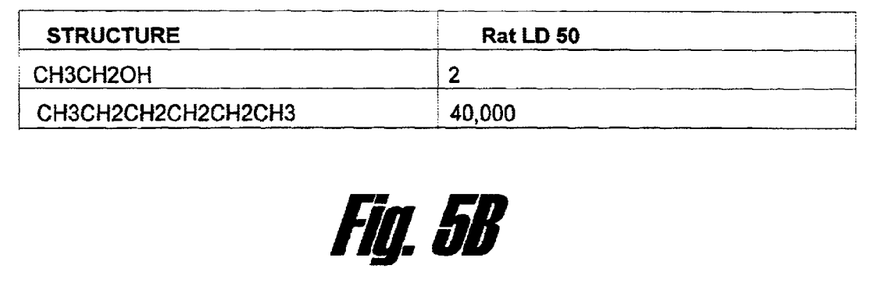
FIG. 5B is a diagram illustrating an example toxicity table for a subset of those compounds listed in the table of FIG. 5A.
Figure 5C:
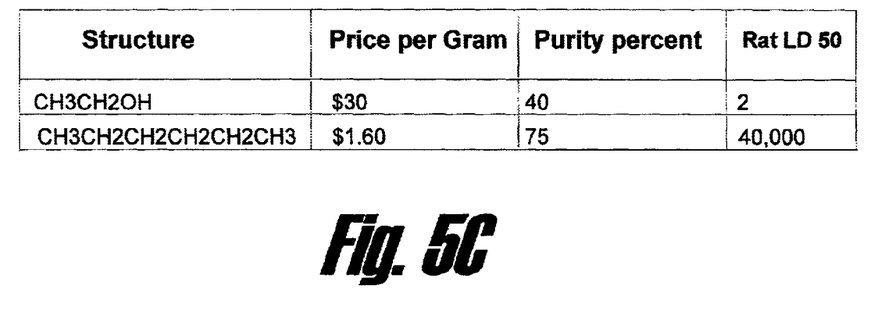
FIG. 5C is a resultant joined table showing the availability of the compounds in the table of FIG. 5A along with the Rat LD50 data of set of compounds in the table illustrated in FIG. 5B.

FIG. 5A is a diagram illustrating an example Vendor table for chemical compounds. FIG. 5B is a diagram illustrating an example toxicity table for a subset of those compounds listed in the table of FIG. 5A. FIG. 5C is a resultant joined table showing the availability of the compounds in the table of FIG. 5A along with the Rat $LD_{50}$ data of set of compounds in the table illustrated in FIG. 5B.

The join illustrated in FIGS. 5A–5C is useful in situations where the structures in the available catalogue have already been tested for the attribute of interest. For the above-described example of toxicology data, this type of join is useful where the toxicology endpoint and that data is in an existing "Toxicity" table. Unfortunately, to date, very few compounds available from commercial vendors or through high-throughput (combinatorial) chemistry have known toxicology data. Thus, using traditional chemical searching catalogues, unless the user happens to search for a specific compound that has been tested for toxicity, it is very unlikely that the user will obtain toxicity information related to the compound of interest. This is a primary reason why a chemical similarity join is an essential feature of our invention.

In this context, our disclosure of a chemical similarity join is exemplary of our disclosure of "fuzzy" similarity join. In a broader context than the exemplary situation, a fuzzy similarity join follows the same logic, ie., by organizing and associating information that is not ordinarily associated or organized together, based upon similarity features between components within a library information integration.

Genomics

A similarity index is defined for two sequences based on the number of conserved bases, or on more sophisticated analysis of the sequences as is exemplified by the FastA or Blast searching systems. The join based on this similarity measure is used to connect sequences of unknown genes or unknown function with databases of well characterized genes. This can help place a new gene in a family or super-family, and assist in identifying its function.

Clinical Trial Population

The candidates for clinical trials can be described by myriad metrics, including standard demographic data, physical characteristics, personality profile tools, driving records, etc. The results of gene profiling may also be used as descriptors in "people-space." A distance measure could be defined in several ways, and would characterize the amount of difference between any two people mapped into this people-space. One example of a distance function is as follows: 1) normalize each people-space metric to the range 0–1 based on the minimum and maximum values in the entire set; 2) calculate the distance as $$d(A,B)=\Sigma \min(A_i B_i)/\max(A_i B_i)$$

This is a generalized form of the Tanimoto coefficient for spaces not limited to parameter values of 0 and 1. Using this similarity measure, a database of potential subjects can be linked to a database of previous testing results in which certain members experienced undesirable side effects. The susceptibility of the new subjects can then be estimated from the previous results based on their similarity to the previous test subjects.

The fuzzy similarity joins, including the exemplary chemical similarity join disclosed herein, can be implemented in various ways, including but not limited to Relational Database Systems, non-relational database systems, filebased information systems, spreadsheet-type systems, or on non-computer-based methods including index cards, paper collection, etc. A preferred embodiment would use the Oracle database system. In Oracle, the fuzzy database join could be implemented as an Oracle cartridge defining the chemical structure as a new entity and the similarity comparison as a new operator acting of the chemical structure entity. The join could also be implemented in Oracle as an external procedure call. In this embodiment, the SQL language for specifying queries would be enhanced to allow the specification of the fuzzy similarity joins along with the other query criteria.

An alternate implementation could involve precalculation of the fingerprint bitmaps or other structurebased metrics and storage of the precalculated metrics in Oracle or in files of systems external to Oracle. Another alternate implementation would involve pre-calculation of the similarity of some or all pairs of structures and storage of the similarity values in Oracle or in an external file or system.

This invention pertains to the "conceptual" joining (i.e., the records are not joined in the manner desired) of records based on fry similarity, whether or not the implementation uses a relational database system such as Oracle, and does not depend on the integration of the query specification of the fuzzy similarity join with the other query criteria.

Referring back to chemical similarity join, we note that although data that would enhance the information value of a primary table is often not available for exactly the same chemical structure, it often is available for similar structures. If the chemical space is defined in such a way that a neighborhood effect exists for the property in question (for example, toxicology), then the property for the compounds in the primary table can be inferred from the property data of similar compounds in the secondary table. This is the basis for a chemical similarity join, because it allows, for example, two tables to be joined not by exact match of the structure, but by the similarity comparison of the two structures.

In a chemical similarity join according to one embodiment, the rows from to two tables are combined in a row in the resultant table if the similarity index for the two compounds is greater than a particular threshold (e.g. 80%). Exemplary properties for which a neighborhood effect exists and thus would allow for a useful chemical similarity join include but are not limited to:

Bio-efficacy—A table generated from the hits of primary screening (all active) can be joined to those in an available chemicals table to find the SAR neighbors that should be tested in secondary screening.

Toxicology data—A table of acquirable compounds can be joined to a table of toxicology data. The resultant table can include for each compound in the primary table the average toxicology data for the neighbors in the toxicity table. This value is an estimate of the toxicology for the primary table compounds and could be used to weed out potentially toxic compounds or to prioritize the testing schedule.

Patent coverage—Some patents may cover specific structures as well as generic descriptions of covered chemicals. The specific structures are often available in databases of patented compounds. It is more difficult to determine if a compound is covered by the generic descriptions, but can be done on a one-by-one basis. A Chemical Similarity Join of an acquirable chemical table with a patent table can be used to produce a count of closely related structures directly covered by a patent. This can represent a "patent-alert flag" —for example, if 20 near-neighbors of a compound are covered by one or more patents, this might signal the user to investigate whether this compound is also covered.

Expandability—If a set of acquirable compounds is joined to a large virtual database (a set of compounds that could be made, but have not been), information about the ability to expand around the compound can be inferred. This is useful for the selection of the primary screening library members or for selection from a hit list of those structures to be followed up. Here, compounds that have at least a few neighbors in "synthesizable"-chemistry-space are more valuable that those that do not. The count of virtual neighbors becomes an Expandability measure. SAR Set Primary Selection—If a set of acquirable compounds is joined to itself (recursive Chemical Similarity Join), each compound in the set can be attributed with the number of neighbors it has. This allows selection of compounds to form the primary screening set that contain small SAR-type clusters.

Figure 6:
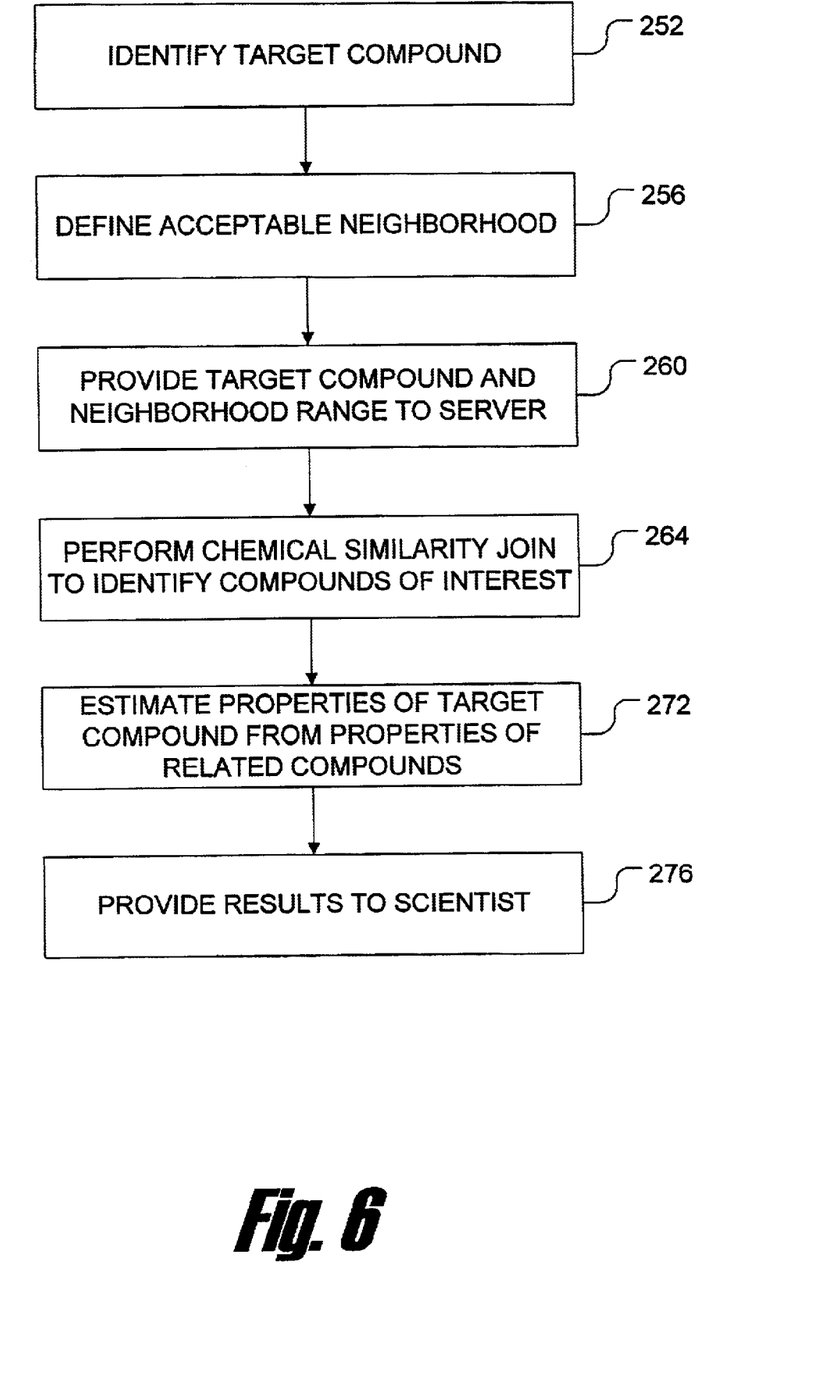
FIG. 6 is an operational flow diagram illustrating a process for identifying potential compounds for a user according to one embodiment of the invention.

Having now disclosed the basis for a chemical similarity join, reference is now made to FIG. 6, an operational flow diagram illustrating a process for identifying potential compounds for a user utilizing a chemical similarity join. In FIG. 6, step 252, a user searching for a compound to meet his or her needs can identify a target compound for which he or she is searching. The user generally will identify a specific compound of interest by chemical structure (although other approaches, e.g., chemical name, can also be utilized).

Because the user desires to search for chemical compounds similar to the identified target compound, in a step 256 the user defines an acceptable neighborhood or range of values for the property metrics of the target compound identified in step 252. The neighborhood can be thought of as a range of chemistry space surrounding the target compound in which a search is acceptable. Alternatively, and as described above with reference to FIGS. 2 and 3, this step is not required as a user may simply choose to look in a predefined neighborhood (for example, a cell-based neighborhood in which the compound resides).

In a step 260, the user provides the target compound and neighborhood range to server 104. These parameters can be submitted to server 104 via the Internet. Forms and other appropriate interfaces in this embodiment can be provided to the users to facilitate their providing this information to server 104.

In a step 264, a chemical similarity join is performed. A variety of techniques can be used to form the basis of the chemical similarity join. For example, Tanimoto coefficients can be utilized to determine similarities between compounds and thereby determine whether a compound is within the selected neighborhood. Molecular holograms can be used to compare two or more molecular structures to determine whether the compounds are within a defined neighborhood. Molecular holograms and their use in QSAR can be found in U.S. Pat. No. 5,751,605 to Hurst et al., which is incorporated herein by reference.

In a step 272, the joined records may be averaged, counted, or processed with other statistical techniques in order to provide an estimate of the properties of the compounds in the primary data set. For example, if the secondary data set contains toxicology data, the average of the toxicology values for the related compounds may be used as an estimate of the toxicology for the primary compound. Alternatively, the detailed information about the related structures and their property values may be returned in total.

In a step 276, server 104 provides the results of this search to the user at his or her workstation 102. As stated above, the user can evaluate the compounds returned as a result of the search and make a decision as to whether to purchase the compound for his or her research purposes. In one embodiment, server 104 can coordinate or even handle the sale of the compound or compounds to the user. In Internet embodiments, for example, server 104 can also include the capability to complete the sale of the compound as a conventional "e-commerce" site. Additionally, the user could be forwarded to another server or another site to make and complete the purchase of the compound.

To further elucidate the various features and aspects of the invention, a few example user scenarios are set forth. These scenarios discuss uses to which one or more embodiments of the invention can be utilized in a research setting. After reading these scenarios it will become apparent to one of ordinary skill in the art how to implement the invention for these and numerous alternative scenarios.

Figure 7:
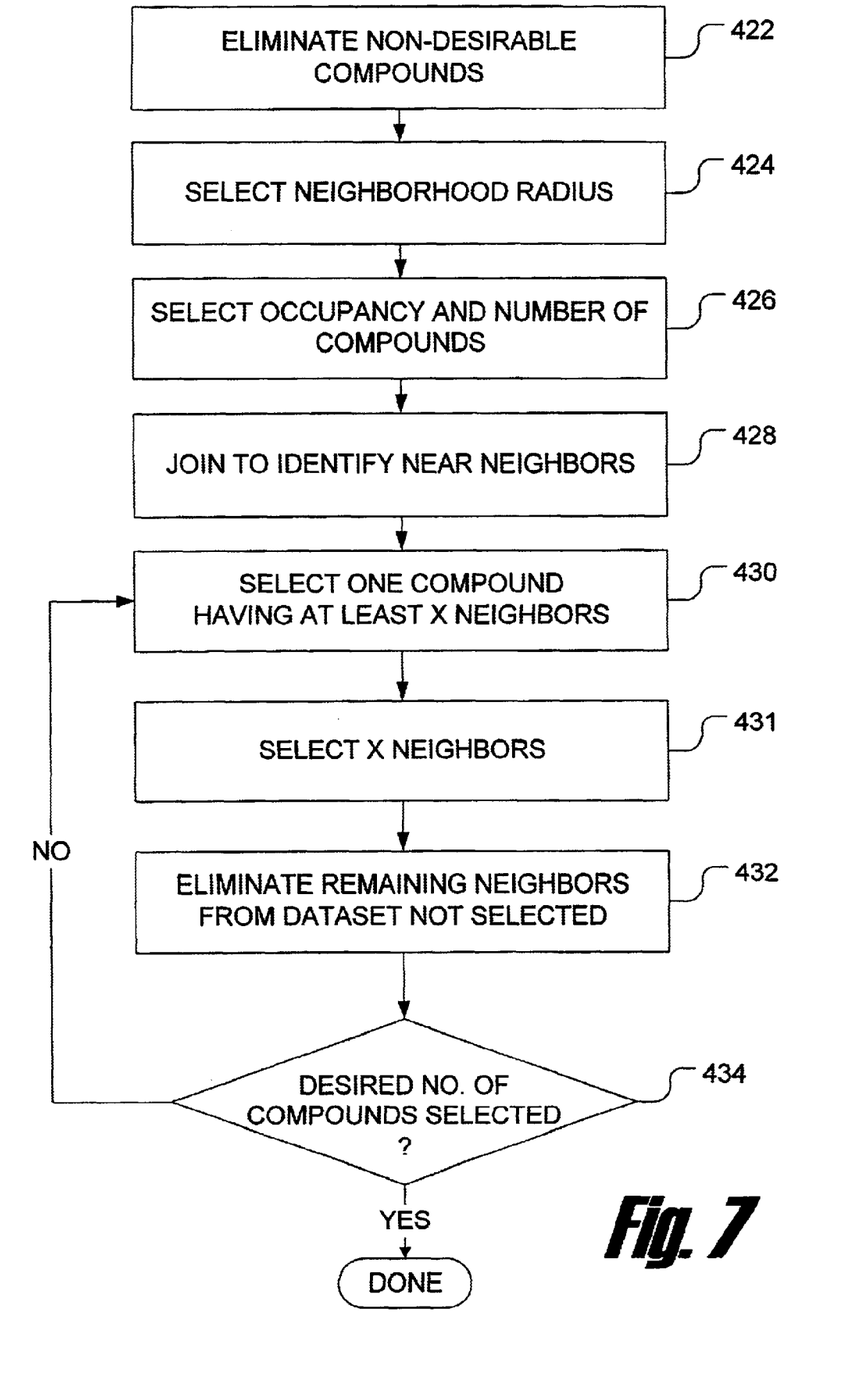
FIG. 7 is an operational flow diagram illustrating an example scenario for primary selection according to one embodiment of the invention.

FIG. 7 is an operational flow diagram illustrating one example scenario by which a user may use the chemical library integration tool to perform primary compound selection from a large library or database of available compounds. First, in this setting, the user may wish to eliminate any non-desirable compounds from the set of compounds that are to be under consideration. This is illustrated by a step 422. In this step, compounds in the set that meet the user-defined criteria for a non-desirable compound are eliminated. For example, the user may decide to eliminate compounds based on the size of the molecules, cLogP ranges, reactive or toxic functional groups, etc. Such exclusion criteria are based upon the particular needs of the user.

In a step 424, the user selects a neighborhood radius to define the similarity range in which he or she wishes to search. In one embodiment, the user selects a radius for SAR clusters. Typically, this range is chosen to be approximately 0.8, or 80%, although other radii can be chosen.

In one scenario, the user may be searching for small SAR clusters in different areas of chemical space. For example, the user may be seeking compound dusters that number about, e.g., 10. Thus, in a step 426, the user selects a desired neighborhood occupancy rate, and indicates the desired total number of compounds that he or she wishes to select in this search process.

In a step 428, the library or database is joined to itself using, for example, a chemical similarity join. This join produces a count of near-neighbors for each compound. Stated again, this join produces a count of the compounds within the defined neighborhood of each compound. The chemical similarity join allows the user to locate compounds that are within the chosen similarity radius.

Having counted compounds within the various neighborhoods, a compound having at least X neighbors is selected along with X or its neighbors and eliminated from the dataset. This selection is made from the set not previously eliminated nor selected. The remaining neighbors are eliminated from the dataset. This is illustrated by steps 430, 431 and 432.

The process of eliminating neighborhoods is continued until the desired number of compounds has been selected for evaluation. This is illustrated by a step 434. Once the desired number of compounds has been selected or there are no more compounds to select, samples of the selected compounds can be ordered by the user for, e.g., biological screening.

Another common practice in the laboratory is that of lead follow-up. This approach is generally utilized when a user follows one or more leads uncovered in a broader search, to determine whether the leads are of sufficient importance to warrant further consideration. FIG. 7 is an operational flow diagram illustrating an example process of using the invention to perform lead follow-up according to one embodiment of the invention.

Figure 8:
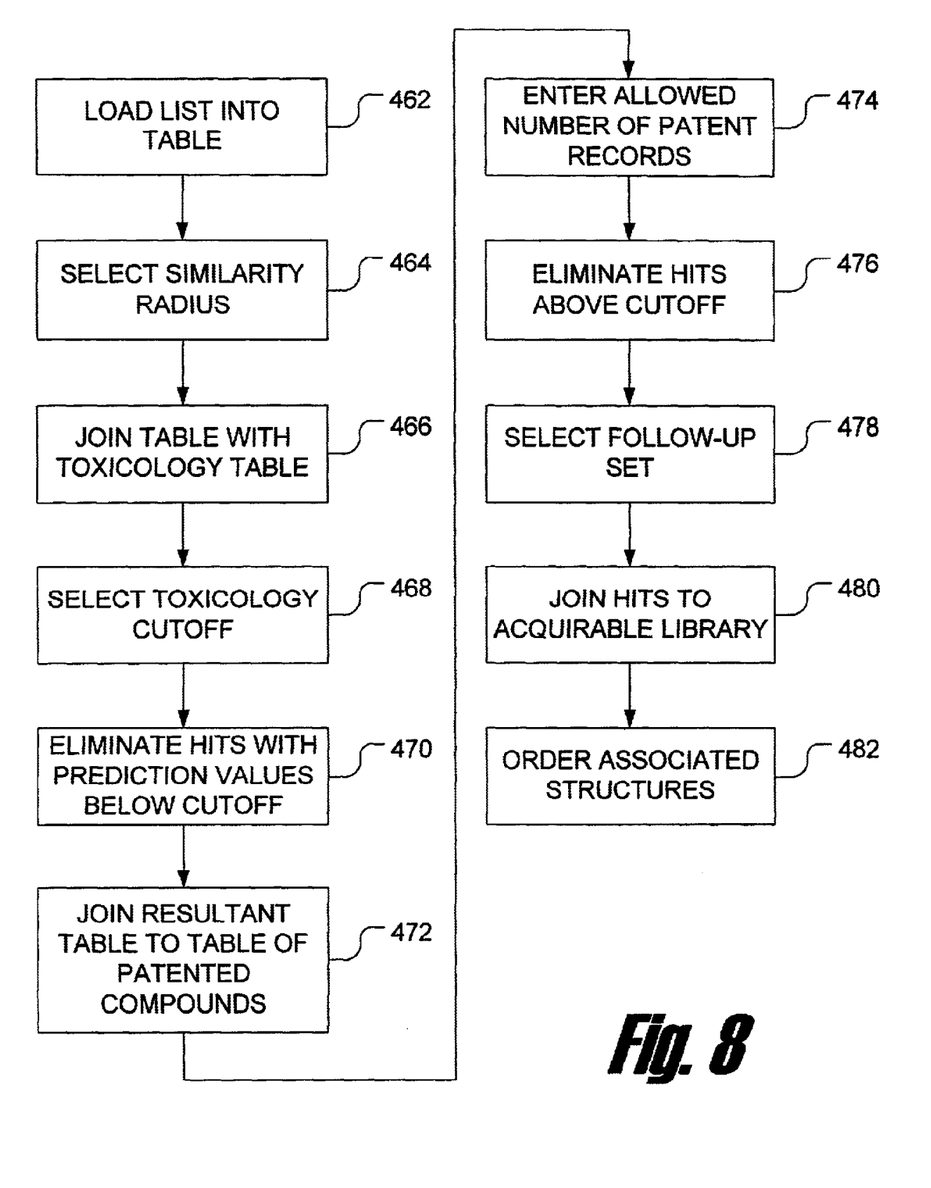
FIG. 8 is an operational flow diagram illustrating an example scenario for lead follow-up according to one embodiment of the invention.

Referring now to FIG. 8, a list of hits from a high-throughput screening are identified and set forth, or "loaded." into a table. This is illustrated by a step 462.

In a step 464, the user selects the desired similarity radius. As with the example scenario described above, one common similarity radius utilized in this process is typically 0.8 or 80%, although other radii can be selected.

In a step 466, the table of hits is joined using a chemical similarity join, with a table of toxicology data. Because a chemical similarity join is used instead of a standard join, the join operation covers compounds in a toxicology table that are within the similarity radius of the subject compound. Stated again, it is not necessary for a successful join operation to occur that the identical compound be found in the toxicology table as well. Instead, the similarity join is broader in that it captures compounds within the defined similarity radius. In this join, the toxicology data for various joined rows is averaged to establish a toxicology prediction for the primary table structures.

In a step 468, the user selects a toxicology cut-off value. For example, the user may define that he or she does not desire compounds with a toxic dose lower than the defined minimum. In a step 470, the hits with toxicology prediction values above the cut-off can be eliminated. That is, in one embodiment, where the chemical similarity join of the subject compound with a toxicology table results in a small, predicted toxic dose, the compound can be eliminated.

In this scenario, the user also considers information pertaining to the patent coverage of potential compounds. Thus, in a step 472, the resultant table is joined to a table of patented compounds to determine the likelihood of patent protection in that area. That is, the compounds remaining after step 470 are joined using a chemical similarity join to a table of patented compounds. In this join, the number of joined records is counted. In a step 474, the user enters the number of patent records that define an acceptable limit. The resultant table is examined to determine the number of compounds within a similarity radius of the subject compounds that are covered or otherwise affected by patents. In a step 476, hits above the cut-off selected by the user can be eliminated.

In a step 478, the user selects a follow-up set. For example, from the compounds remaining after the above-described similarity joins, the user may choose 10 or so compounds to perform more extensive testing. In a step 480, the selected compounds are joined to a library of acquirable chemicals. Again, the compounds are joined using a chemical similarity join. In one embodiment, this join can be accomplished using an inner join, with no averaging or counting. In a step 482, the associated structures are ordered, e.g., for secondary screening.

As these scenarios illustrate, one advantage of using a chemical similarity join is that data about chemicals or compounds within a similarity radius can be used to predict or infer behavior, attributes, or other parameters associated with the subject compound for which the similarity join is being performed. For example, a user may wish to have information regarding toxicity and patent coverage for a given compound, or for a virtual compound. However, this data may not exist for that particular compound or virtual compound. Thus, a standard relational database join operation would not provide information about these parameters to the user. However, using a chemical similarity join that performs the join operation within a similarity radius allows the user to obtain and study information that may be in existence pertaining to compounds within the defined similarity radius. The user can then use this information to infer or predict whether these parameters will be present in the selected compound or virtual compound.

The various embodiments, aspects, and features of the invention described above may be implemented using hardware, software, or a combination thereof and may be implemented using a computing system having one or more processors. In fact, in one embodiment, these elements are implemented using a processor-based system capable of carrying out the functionality described with respect thereto.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A computer-based method for facilitating the selection of chemical compounds, comprising:

receiving an identification of a target compound and a neighborhood range from a user;

performing a chemical similarity join to identify compounds of interest within said neighborhood range of said target compound, said chemical similarity join being performed on:
  a first database table that stores information about one or more compounds including said target compound; and
  a second database table that stores information about a plurality of compounds, wherein said chemical similarity join combines a compound from said first database table with a compound from said second database table and the compound from the second database table is within said neighborhood range; and
providing results of said chemical similarity join to the user.

* * * * *